United States Patent [19]

Allen

[11] 4,332,742
[45] Jun. 1, 1982

[54] LOW TEMPERATURE STORAGE STABLE LIQUID DIPHENYLMETHANE DIISOCYANATES

[75] Inventor: Gary F. Allen, New Martinsville, W. Va.

[73] Assignee: Mobay Chemical Corporation, Pittsburgh, Pa.

[21] Appl. No.: 276,144

[22] Filed: Jun. 22, 1981

[51] Int. Cl.³ .......................................... C07C 119/048
[52] U.S. Cl. ........................ 260/453 SP; 260/453 AM
[58] Field of Search .................. 260/453 SP, 453 AM

[56] References Cited

U.S. PATENT DOCUMENTS 3,394,165  7/1968  McClellan et al. ............ 260/453 SP
3,787,469  1/1974  Davis et al. .................... 260/453 A Primary Examiner—Dolph H. Torrence
Attorney, Agent, or Firm—Gene Harsh; Joseph C. Gil

[57] ABSTRACT

The present invention is directed to a room temperature storage stable liquid isocyanate comprising the reaction product of a diphenylmethane diisocyanate and an N-substituted ethanolamine of the formula:

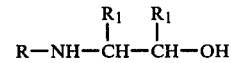

wherein R represents a $C_6$–$C_{10}$ aryl and wherein at least one $R_1$ represents hydrogen and the other $R_1$ is selected from the group consisting of hydrogen, $C_1$ to $C_3$ alkyl and phenyl.

7 Claims, No Drawings

LOW TEMPERATURE STORAGE STABLE LIQUID DIPHENYLMETHANE DIISOCYANATES

BACKGROUND OF THE INVENTION

It is well known that diisocyanates which are liquid at room temperature (i.e., about 25° C.) have numerous advantages over solid diisocyanates because they are easier to mix and work with. However, diisocyanates which are liquid at room temperature and which are used on a large technical scale, such as toluene diisocyanate or hexamethylene diisocyanate, are as a rule physiologically harmful due to their high vapor pressure and, therefore, can only be used if certain safety precautions are taken. For this reason, various attempts have been made, either to start with diisocyanates that are normally liquid at room temperature and to reduce their physiological effects by certain procedures or to start with diisocyanates that are solid at room temperature and to convert these into liquid form. In both cases, however, one usually obtains either isocyanates of higher valency, i.e., tri- or polyisocyanates or higher molecular weight diisocyanates or a combination of these effects.

The most important diisocyanates which are solid at room temperature and which are readily available on a large commercial scale are 4,4'-diphenylmethane diisocyanate and the 2,4'-isomer thereof which melt at 39° C. and 34.5° C., respectively. Attempts have already been made to liquefy both the 4,4'-diphenylmethane diisocyanate and a mixture of the 4,4'-diphenylmethane diisocyanate and a small amount of the 2,4'-isomer. Thus, for example, in U.S. Pat. No. 3,644,457, 1 mol of a diphenylmethane diisocyanate is reacted with from about 0.1 to about 0.3 mols of poly-1,2-propylene ether glycol. While the products made according to this patent have met with commercial success, they still suffer from a serious drawback. Specifically, it has been found that these adducts generally will crystallize anywhere from 5° C. to as high as 25° C. In fact, when supplied in commercial quantities, these adducts are generally transported in heated trucks. Additionally, in order to thaw the materials, it is generally necessary to heat them to somewhere in excess of 50° to 60° C. While in warmer climates, there may not be any problem, in colder areas where the product may be stored in tanks over a period of time, this tendency to crystallize can become a very serious problem. Similar attempts to form liquid diphenylmethane diisocyanates have been described, for example, in U.S. Pat. Nos. 3,384,653; 3,449,256 and 3,394,164. The attempts to liquefy in these instances were based on the addition of, in one case, a trihydrocarbyl phosphate and, in the other case, small amounts of phosphoric acid. In any event, the storage stability of both of these types of products is again quite good around room temperature, but as the temperature decreases, both types of materials tend to crystallize.

There are numerous other patent references relating to the production of liquid diphenylmethane diisocyanates. Some of the approaches taken include the reaction of the isocyanate with N,N-di(2-hydroxypropyl) aniline in the presence of phosphoric acid (U.S. Pat. No. 3,394,165); the introduction of carbodiimide groups into the isocyanate (U.S. Pat. Nos. 4,177,205; 3,641,093; 3,640,966; 4,014,935; 3,152,162; 4,088,665; 4,072,712; 4,143,063 and 4,154,752); and the reaction of the isocyanate with (i) polyoxyethylene glycols (U.S. Pat. Nos. 4,115,429 and 4,055,548); (ii) propylene glycols (U.S. Pat. Nos. 4,118,411 and 3,892,691); (iii) N,N'-disubstituted thioreaus (U.S. Pat. Nos. 3,674,828); and (iv) low molecular weight polyether polyols (U.S. Pat. No. 4,102,833). Other approaches include the addition of an organosilicone (U.S. Pat. No. 3,585,230); the addition of a dibenzoate (U.S. Pat. No. 3,701,796); and the combination of partial carbodiimidization with a reaction product of the isocyanate and a diol (U.S. Pat. No. 4,031,026). It is apparent that the art is continuing its search for commercially acceptable liquid diphenylmethane diisocyanates.

One of the currently used methods of producing a liquid diphenylmethane diisocyanate involves the reaction of difunctional polypropylene glycol with diphenylmethane diisocyanate (see, e.g., U.S. Pat. No. 3,644,457). The resultant liquid product consists of unreacted diphenylmethane diisocyanate and various adducts of the glycol with the isocyanate. The adducts are generally those produced from two mols of isocyanate and one mol of glycol, three mols of isocyanate and two mols of glycol, four mols of isocyanate and three mols of glycol, and higher adducts. The freezing point depression of the isocyanate caused by the presence of the adducts can be varied by adjusting the number of adducts. In general, as the amount of adduct molecules increases, the freezing point decreases and the viscosity increases. Necessarily, practical constraints are placed on the amount of glycol that can be added such that the product is liquid while, at the same time, the product has a low enough viscosity for ease of processing.

The adducts formed as defined above must be significantly soluble in the isocyanate. Short chain diols, such as ethylene glycol, 1,4-butane diol and 1,6-hexane diol, form adducts with diphenylmethane diisocyanate which are insoluble in the diisocyanate and precipitate from solution at 45° C. (i.e., above the melting point of the isocyanate itself). Adducts of these types of diols can be made soluble by using a diol having alkyl-substitution and by using a diol having oxygen linkages in the backbone. It appears that both ether linkages and alkyl substitution are necessary. Thus, 1,3- and 2,3-butane diol and diethylene glycol form solids or gels when reacted with excess diphenylmethane diisocyanate, while di- and tripropylene glycol form liquids with such isocyanate.

It is also known that the introduction of urea linkages in a polyurethane polymer has an advantageous effect including increasing stiffness, improving high temperature properties and improving tensile strength. However, it has not been thought that a urea group could be incorporated in a diphenylmethane diisocyanate while at the same time producing a liquid product.

It is, therefore, an object of this invention to provide improved liquid organic diisocyanates which are liquid and stable at temperatures even lower than room temperature. A further object of this invention is to provide organic diisocyanates which remain liquid even on storage at low temperatures. It is yet a further object of the present invention to produce a liquid isocyanate which contains urea linkages.

DESCRIPTION OF THE INVENTION

The instant invention is directed to novel isocyanate compounds which are stable and liquid at temperatures at or lower than room temperature. The isocyanate compounds of the invention have isocyanate contents of from 20 to 27% by weight and comprise the reaction product of a diphenylmethane diisocyanate with an N-substituted ethanolamine. The materials are reacted in an NCO/OH equivalent ratio of from about 3:1 to about 15:1, preferably from about 3:1 to about 10:1, and most preferably from about 3:1 to about 6:1.

The N-substituted ethanolamine and the isocyanate can be reacted at temperatures ranging anywhere from room temperature (i.e., about 25° C.) up to about 125° C. Preferably, the reaction temperature is from room temperature to about 90° C., and most preferably from about 40° C. to about 80° C.

The diphenylmethane diisocyanates usable according to the present invention generally contain the 4,4′-isomer, the 2,4′-isomer and/or the 2,2′-isomer and may contain small amounts of higher oligomers of diphenylmethane diisocyanate.

The liquid diisocyanates which can be prepared according to the instant invention have a relatively low viscosity and can, therefore, be worked up very easily, e.g., they can be cast or metered through pumps. In addition, they have a very low vapor pressure and are, therefore, substantially physiologically harmless. Since the reaction can generally be carried out at relatively low temperatures, the diisocyanate structure of the product of the process is completely preserved. Allophanate formation by the reaction of the resulting urethane groups with the isocyanate group to produce a polyisocyanate apparently does not take place to any large degree. This is true even when forming the reaction product at a temperature of 125° C.

The N-substituted ethanolamines useful according to the present invention correspond to the following general formula:

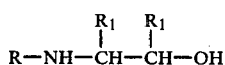

wherein R is a $C_6$-$C_{10}$ aryl and wherein the $R_1$'s are the same or different and represent $C_1$-$C_3$ alkyl, phenyl, a hydrogen, at least one $R_1$ being hydrogen; R is preferably phenyl and one $R_1$ is preferably hydrogen while the other is either hydrogen or phenyl. The most preferred compound is N-phenyl ethanolamine.

The process of the instant invention may be carried out by introducing the amine into the diisocyanate at temperatures of from room temperature up to about 125° C. with stirring. Alternatively, the diisocyanate can be introduced into the amine. The isocyanate content of the products of the process generally amounts to from about 20% to as high as about 27%.

The N-substituted ethanolamines of the present invention may also be blended with other hydroxy functional materials. The hydroxy functional material does not form a liquid product with the diphenylmethane diisocyanate, the N-substituted ethanolamine should be used in an amount of at least 50% by weight based on the weight of the ethanolamine and the additional hydroxy functional material. Where the hydroxy functional material to be added does form a liquid adduct with diphenylmethane diisocyanate, as little as 10% by weight of the ethanolamine can be used. When such mixtures are used, the NCO/OH equivalent ratio should be within the ranges earlier set forth. It is generally preferred, however, that the ethanolamine be used alone.

The products of the process can be used for all types of different polyaddition reactions in the lacquer and plastics industries, e.g., for the production of polyurethane foams or polyurethane elastomers which are, in turn, useful for the preparation of cushions or gear wheels, respectively. The products may be used as the sole isocyanate component in the manufacture of polyurethane or they may be blended with other isocyanates. Because of their low freezing point, the materials can be transported and stored at relatively cold temperatures.

The invention is further illustrated by the following Examples in which all parts are by weight unless otherwise specified.

EXAMPLES

Examples 1-4

To a reactor containing 300 parts of 4,4′-diphenylmethane diisocyanate and fitted with stirrer, heating mantle and nitrogen purge was added about 49 parts of N-phenylethanolamine. The reaction was complete after one hour at 60° C. The resultant product was liquid at room temperature, had an NCO content of about 21% and a viscosity of 13,200 cPs at 25° C.

In a similar manner, the amounts of 4,4′-diphenylmethane diisocyanate (MDI) and N-phenyl-ethanolamine (NPEA) shown in Table I were reacted. The products were all liquid at room temperature, and had the NCO contents and viscosities noted in Table I.

TABLE I

| Example | PBW MDI | PBW NPEA | NCO Content | cPs Viscosity @ 25° C. |
|---|---|---|---|---|
| 2 | 216 | 26 | 23.6 | 875 |
| 3 | 240 | 24 | 24.5 | 455 |
| 4 | 226 | 17 | 26.4 | 143 |

What is claimed is:

1. A room temperature storage stable liquid isocyanate comprising the reaction product of a diphenylmethane diisocyanate and an N-substutited ethanolamine of the formula:

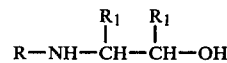

wherein R represents a $C_6$ to $C_{10}$ aryl and wherein at least one $R_1$ represents hydrogen and the other $R_1$ is selected from the group consisting of hydrogen, $C_1$ to $C_3$ alkyl and phenyl.

2. The isocyanate of claim 1 having an NCO content of from 20 to 27% by weight.

3. The isocyanate of claim 1 wherein the diisocyanate and the ethanolamine are reacted at an NCO to OH equivalent ratio of from about 3:1 to about 15:1.

4. The isocyanate of claim 3 wherein the diisocyanate and the ethanolamine are reacted at an NCO to OH equivalent ratio of from about 3:1 to about 10:1.

5. The isocyanate of claim 4 wherein the diisocyanate and the ethanolamine are reacted at an NCO to OH equivalent ratio of from about 3:1 to about 6:1.

6. The isocyanate of claim 5 having an NCO content of from 20 to 27% by weight.

7. The isocyanate of claim 3 wherein said ethanolamine is N-phenylethanolamine.

* * * * *